United States Patent [19]

Wiegleb

[11] Patent Number: 4,900,152
[45] Date of Patent: Feb. 13, 1990

[54] APPARATUS FOR MEASURING FOREIGN SUBSTANCE CONTENT IN A FLOWING LIQUID

[75] Inventor: Gerhard Wiegleb, Geiselbach, Fed. Rep. of Germany

[73] Assignee: Leybold Aktiengesellschaft, Cologne, Fed. Rep. of Germany

[21] Appl. No.: 151,444

[22] Filed: Feb. 2, 1988

[30] Foreign Application Priority Data

Nov. 23, 1987 [DE] Fed. Rep. of Germany ....... 3739589

[51] Int. Cl.⁴ ...................... G01N 21/11; G01N 21/15
[52] U.S. Cl. ................................... 356/411; 250/576; 356/435; 356/440
[58] Field of Search ............... 356/410, 411, 436, 440, 356/440, 435; 250/575, 576, 430, 431, 432 R

[56] References Cited

U.S. PATENT DOCUMENTS 4,303,337 12/1981 James et al. ........................... 356/72
4,608,159 8/1986 Collins, Jr. .......................... 210/101

FOREIGN PATENT DOCUMENTS 55-116243 9/1980 Japan .................................. 356/410

OTHER PUBLICATIONS

Patent Abstracts of Japan (M-78) (4590); JP-A-5310 7578 (Hita Chi Salsakusho), 19.9.1978.
Burrows, "Application of IR and UV Analyzers to On Stream Analysis", Advances in Instrumentation, Oct. 1985, Research Triangle Park, N.C., U.S.A., pp. 1357-1385.

Primary Examiner—Vincent P. McGraw
Attorney, Agent, or Firm—Felfe & Lynch

[57] ABSTRACT

In an apparatus for determining the concentration of foreign matter in a water stream, a stream of liquid is bypassed through conduits both before and after the pipeline block for the process and each stream is pumped into a cell, a beam source being associated with each of the cells whose beams penetrate the cells and are led by a beam splitter both to a first detector and to a second detector, the electrical signals of the detectors being compared by an electrical circuit and processed to a recognition signal. To make a bubble-free sample stream possible, magnetically actuated valves are inserted into the return lines which are connected to the cells, and the signals for opening and closing the valves are produced by a frequency generator.

2 Claims, 1 Drawing Sheet

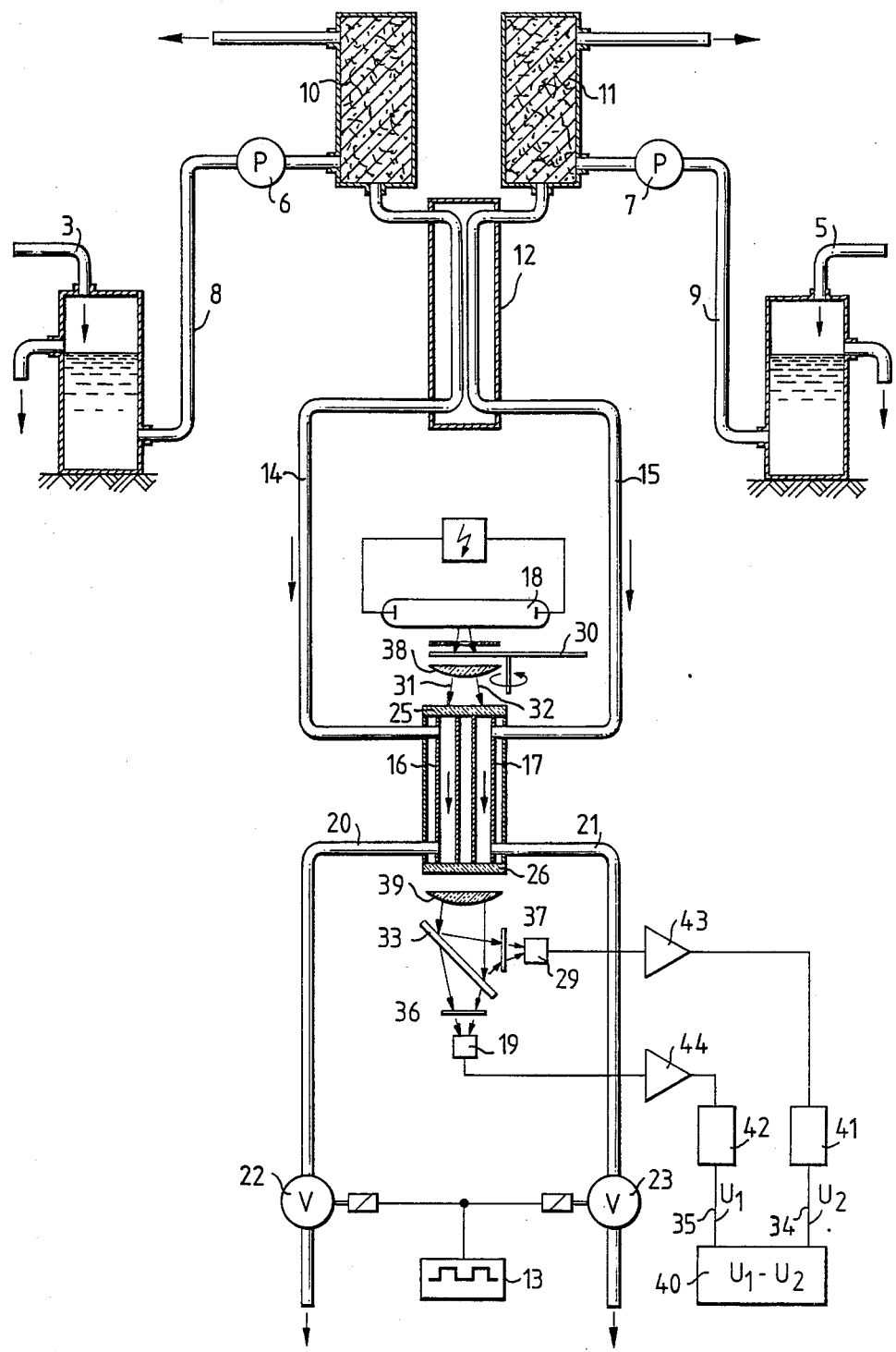

APPARATUS FOR MEASURING FOREIGN SUBSTANCE CONTENT IN A FLOWING LIQUID

BACKGROUND OF THE INVENTION

The invention relates to an apparatus for measuring foreign substance content in a flowing liquid, with a stream of liquid bypassed for the process through a conduit. The stream is pumped into a cell, and with the cell a beam source is associated whose beam penetrates the cell and is fed to a detector, and the electrical signal of the detector is processed by an electrical circuit to a recognition signal, in accordance with DE No. 37 335 73, to which EP No. 310740 corresponds.

Apparatus are known for measuring the foreign substance content in a gas stream, and are used for process control in chemical plants, for flue gas measurement and for measuring emissions from boiler firing and from motor vehicles. These known apparatus operate on the nondispersive ultraviolet absorption principle of measurement. The specific absorption of radiation by the component being measured serves as the effect that is utilized.

The ultraviolet radiation is produced in a hollow cathode lamp. A rotary shutter divides the beam into two beams that are separated in time, and a beam splitter divides it into two beams separated in space. The beam that is measured is passed through the cell and strikes a receiver. The completely unaffected beam used for comparison strikes the correction receiver.

The electronic processing of these four signals eliminates the influence of nonselective absorptions, such as cell soiling and aging effects in the radiators and receivers.

SUMMARY OF THE INVENTION

It is the aim of the present invention to improve an apparatus of the type described above by eliminating gas bubbles in the sample stream. The apparatus is to be economical to manufacture and above all it must also be able to be retrofitted into apparatus already available.

This aim is achieved according to the invention by the fact that a valve which is electrically actuated is inserted into that a valve which is electrically actuated is inserted into the liquid return flow conduit connected to the cell, the signal for the abrupt opening or closing of the valve being produced by a signal source, such as a frequency generator for example.

BRIEF DESCRIPTION OF THE DRAWING

The sale figure diagrammatically shows the circuit diagram for an apparatus for the continuous determination of the benzene content in running water.

DETAILED DESCRIPTION OF THE PREFERRED EMBODIMENT the apparatus consists essentially of a pipeline 3 carrying comparatively clean input water, a pipeline block needed for a process, which is not shown in detail, a pipeline 5 carrying discharged water possibly contaminated by the process, the two bypass lines 8 and 9 and the pumps 6 and 7 inserted therein, the two fiber filters 10 and 11, the heat exchanger 12 connected to the output of the fiber filters 10 and 11, the bypass lines 14 and 15 which are connected to the cells 16 and 17, the light source 18 and the detectors 19 and 29, the two discharge lines 20 and 21, the magnetic valves 22 and 23 inserted into the discharge lines, and lastly the frequency generator 13 and the signal processor with the amplifiers 43 and 44 and the filters 41 and 42.

The apparatus operates as follows: from the input water flowing to the pipeline block a stream of water is bypassed from the pipeline 3 through the bypass line 8 from the pump 6, and it is then pumped into the fiber filter 10 and from there into the heat exchanger 12. The stream of water, rendered largely bubble-free by the fiber filter 10 and with its temperature adjusted, is then pumped through the cell 16 and then into the discharge line 20. At the same time a second stream of water is bypassed from the discharged water through the branch line 9 and is then forced by the pump 7 into the fiber filter 11 and the heat exchanger 12 and on into the second cell 17, and then into the discharge line 21.

An ultraviolet light source is associated with the two cells 16 and 17 and its beams penetrate through the cells 16 and 17 and the water present therein, since the front and back end walls 25 and 26 of the cells 16 and 17 are made of translucent material.

Between the cells 16 and 17 and the ultraviolet light source a perforated disk 30 driven by a motor rotates such that the beams 31 and 32 alternately fall on a semitransparent mirror 33 which directs them onto the detectors 19 and 29. Before each detector 19 and 29 there is placed a light filter 36 and 37, respectively, for 254 nm and 298 nm wavelengths, for example. Furthermore, condenser lenses 38 and 39, respectively, are provided which direct the beams 31 and 32 to the respective detectors 19 and 29. The electrical signals produced by the two detectors are processed in the electrical circuit 41 and 44 to signals which go to the electrical conductors 34 and 35 and thus to the display 40.

The circuit itself has RC filters 41 and 42 and amplifier components 43 and 44 which process the electrical signals delivered by the detectors 19 and 29.

While the two water streams are being pumped uniformly by the pumps 6 and 7 through the cells 16 and 17 the chopper wheel 30 rotates at uniform speed so that for each chopper revolution four measurements can be made in parallel.

the chopper 30 alternately opens the path of the beams between the sample side 17 and the reference side 16, while the signals for the specific absorption and the nonspecific absorption are determined synchronously by the two detectors 19 and 29.

In the area where the above-described photometric analysis of liquids is made, in which the sample being analyzed is pumped through analysis cells 16 and 17, in order to detect changes in the transmission of the sample, any bubbling within the cells 16 and 17 must be suppressed. Especially in the analysis of water, in which a certain amount of air is always dissolved, the solution of this problem is especially important.

In the apparatus described, pressure-pulse pumping of the sample to be analyzed successfully prevents the formation of fresh bubbles. Bubbles which are already present ahead of this unit can be removed by a bypass filtration 10 and 11.

In the output from the cells 16 and 17 are magnetic valves 22 and 23 which interrupt the flow at the same rate as the actuation (approximately 1 Hz). If a bubble is present in one of the cells, this bubble is held against the cell wall by forces of adhesion. By closing the valve 22 or 23, this bubble is then compressed to a smaller volume. By the abrupt expansion in a third phase the bubble is carried away by the flow that simultaneously rises abruptly, so that in the final phase no bubble is any longer present.

Bubbles which are situated in a "dead water region" within the cells 16 and 17 are also removed from the cells by this measure.

I claim:

1. In an apparatus for measuring the foreign matter content in a flowing liquid, wherein a reference stream and a sample stream of liquid are each shunted through respective separate conduits (14, 15) and uniformly advanced by means of pumps (6, 7) to cells (16, 17) and thence to discharge lines (20, 21), a light source (18) being associated with said cells (16, 17), the beams (31, 32) from said light source penetrating said cells (16, 17) and traveling to detectors (19, 29) whereupon electrical signals are formed, said electrical signals of said detectors (19, 29) being then processed and compared by electrical circuits 941 to 44) to a recognition signal, the improvement comprising use of a pressure pulse pumping closed system wherein electrically and/or pneumatically controlled valves (22, 23) are inserted into the respective discharge lines (20, 21) for the reference stream and the sample stream, both valves independently opening and closing in rapid succession, the flow in said cells (16, 17) being interrupted at the rate of actuation based upon a signal produced by a frequency generator.

2. The apparatus defined in claim 1 wherein the actuation of the valves (22, 23) takes place at the rate of approximately 1 Hz.

* * * * *